(12) United States Patent
Steen

(10) Patent No.: US 10,987,215 B2
(45) Date of Patent: Apr. 27, 2021

(54) HYDRAULICALLY ASSISTED LENS DELIVERY SYSTEM AND METHOD

(71) Applicant: JOHNSON & JOHNSON SURGICAL VISION, INC., Santa Ana, CA (US)

(72) Inventor: Mark E. Steen, Santa Ana, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 367 days.

(21) Appl. No.: 15/960,435

(22) Filed: Apr. 23, 2018

(65) Prior Publication Data

US 2019/0321162 A1 Oct. 24, 2019

(51) Int. Cl.
| | | |
|---|---|---|
| *A61F 2/16* | (2006.01) | |
| *A61F 9/007* | (2006.01) | |
| *F15B 15/20* | (2006.01) | |
| *A61B 17/00* | (2006.01) | |
| *F16K 31/62* | (2006.01) | |

(52) U.S. Cl.
CPC .............. *A61F 2/167* (2013.01); *A61F 9/007* (2013.01); *A61B 2017/00438* (2013.01); *A61B 2017/00539* (2013.01); *F15B 15/202* (2013.01); *F16K 31/62* (2013.01)

(58) Field of Classification Search
CPC ......... A61B 2017/00539; A61F 2/1662; A61F 2/167
See application file for complete search history.

(56) References Cited

U.S. PATENT DOCUMENTS

| | | |
|---|---|---|
| 4,681,102 A | 7/1987 | Bartell |
| 8,758,433 B2 | 6/2014 | Cole et al. |
| 9,402,716 B2 | 8/2016 | Novak et al. |
| 2008/0255579 A1 | 10/2008 | Wollenhaupt et al. |
| 2015/0342726 A1* | 12/2015 | Deacon ................. A61F 2/1662 623/6.12 |
| 2016/0331516 A1 | 11/2016 | Novak |
| 2017/0071787 A1* | 3/2017 | Canelli ................. A61F 9/0017 |
| 2018/0333253 A1* | 11/2018 | Zakay ..................... A61F 2/167 |

FOREIGN PATENT DOCUMENTS

| | | |
|---|---|---|
| WO | 2015144890 A1 | 10/2015 |
| WO | 2016172113 A1 | 10/2016 |

OTHER PUBLICATIONS

International Search Report and Written Opinion for Application No. PCT/IB2019/053135, dated Jul. 22, 2019, 16 pages.

* cited by examiner

*Primary Examiner* — Sarah A Simpson
(74) *Attorney, Agent, or Firm* — Johnson & Johnson Surgical Vision, Inc.

(57) ABSTRACT

The invention relates to an apparatus and method that provides hydraulically assisted delivery of intraocular lenses (IOL) from a insertion tool. The IOL insertion system having an insertion rod with a tube having a first end and a second end, a piston head affixed to the insertion rod and positioned between the first and second end, a hydraulic chamber, an aspiration line communicatively connected to the hydraulic chamber, and at least one valve in fluid communication with the aspiration line, wherein the insertion rod moves in response to the displacement of hydraulic fluid within the hydraulic chamber.

20 Claims, 3 Drawing Sheets

HYDRAULICALLY ASSISTED LENS DELIVERY SYSTEM AND METHOD

BACKGROUND

Field of Invention

The present disclosure relates generally to medical apparatuses and methods that provide for the emplacement of intraocular lenses during ophthalmic surgery, and more particularly, to medical apparatuses and methods that provide hydraulically assisted delivery of intraocular lenses from an insertion tool.

Description of Related Art

The invention relates generally to the field of intraocular surgery, and more particularly to emplacement of intraocular lenses, such as during phacoemulsification cataract surgery. More particularly, the present system and method provides enhanced control and stability, can be relatively easily and effectively manufactured, and is useful for inserting a foldable intraocular lens into an eye.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic which extends from the optic and becomes affixed in the eye to secure the lens in position. The optic normally includes an optically clear lens. Implantation of such IOLs into the eye involves making an incision in the eye, through which an IOLs, which are known to be foldable (deformable), may be inserted through the incision into the eye through the distal end of the insertion tool. A number of instruments have been proposed to aid in inserting such a foldable lens in the eye.

For example, an IOL may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL to be rolled or folded for insertion through an injector or insertion cartridge and an incision into the eye. Once within the chamber of the eye, the IOL is expulsed from the injector and returns to its original shape.

Injectors or inserters for delivering IOLs into the eye typically employ a handpiece and a removable cartridge that receives the IOL and has a hollow insertion tube or cannula through which the folded IOL is passed using a push rod. The inserter may be wholly or partly reusable, in which case the inserter or handpiece is usually made of some type of metal alloy that can be sterilized. Alternatively, disposable inserters made of less expensive materials, such as plastics, remain in a sterile package until ready for use. In many cases, the IOL may be stored separately and transferred to a load chamber in the inserter or cartridge just prior to delivery. One particularly useful arrangement wherein the cartridge folds over an IOL is disclosed in U.S. Pat. No. 4,681,102 to Bartell. A cartridge opens to receive an IOL in a load chamber, and then folds closed and fits into an injector. A syringe-like plunger in the injector pushes the IOL from the load chamber through a tapered tube into the eye. The IOL unfolds as it emerges from the tip of the tapered tube.

To assist the movement of the plunger, some current systems employ a screw style plunger for both manual and automated delivery. However, electric screw drive motors, particularly associated with automated drives, may be too heavy and oddly shaped to be effectively associated with a surgical handpiece. For these reasons, automation via mechanical means is not widely used.

At least one factor which has historically determined the minimum diameter of the inserter tube at the distal end of the insertion tool and involves the inserter tube itself. For example, the material from which the inserter tube is made, such as polypropylene and the like polymeric materials, may have a relatively high coefficient of friction, causing it to provide a relatively high amount of resistance to an optic made, for instance, from silicone polymeric materials, as it passes through the tube. The amount of resistance, and thus the amount of force (torque) required to pass an IOL through the tube, increases as the diameter of the tube decreases. Since increased torque on the IOL increases the difficulty of controlling the amount and consistency of force on the IOL, it is desirable to reduce, for example, the amount of force required to operate the system.

While many of the prior art inserters include mechanisms to improve control during the IOL insertion process, such as by providing a screw-based plunger, for example, further improvements to the control and ease of IOL insertion are desirable. Accordingly, it would be advantageous to an IOL insertion apparatus which facilitates the passage of folded IOLs through the apparatus in a controlled manner without using excessive force. It would also be advantageous to devise cost-effective and simple methods of making and using insertion apparatus. The subject matter described herein satisfies this need.

SUMMARY

The disclosure relates to an intraocular lens insertion system comprising, an insertion rod comprising a tube having a first end and a second end, a piston head affixed to the insertion rod and positioned between the first and second end, a hydraulic chamber, an aspiration line communicatively connected to the hydraulic chamber, and at least one valve in fluid communication with the aspiration line, wherein the insertion rod moves in response to the displacement of hydraulic fluid within the hydraulic chamber.

The present invention provides for a method of inserting an IOL, the method comprising, applying a first force on an insertion rod comprising a tube having a first end and a second end, and applying a second force on the insertion rod, wherein the first force is applied at the first end of the insertion rod and the second force is applied at a piston head affixed to the insertion rod, and wherein the second force is created by hydraulic pressure.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts.

DETAILED DESCRIPTION

Figure 1:
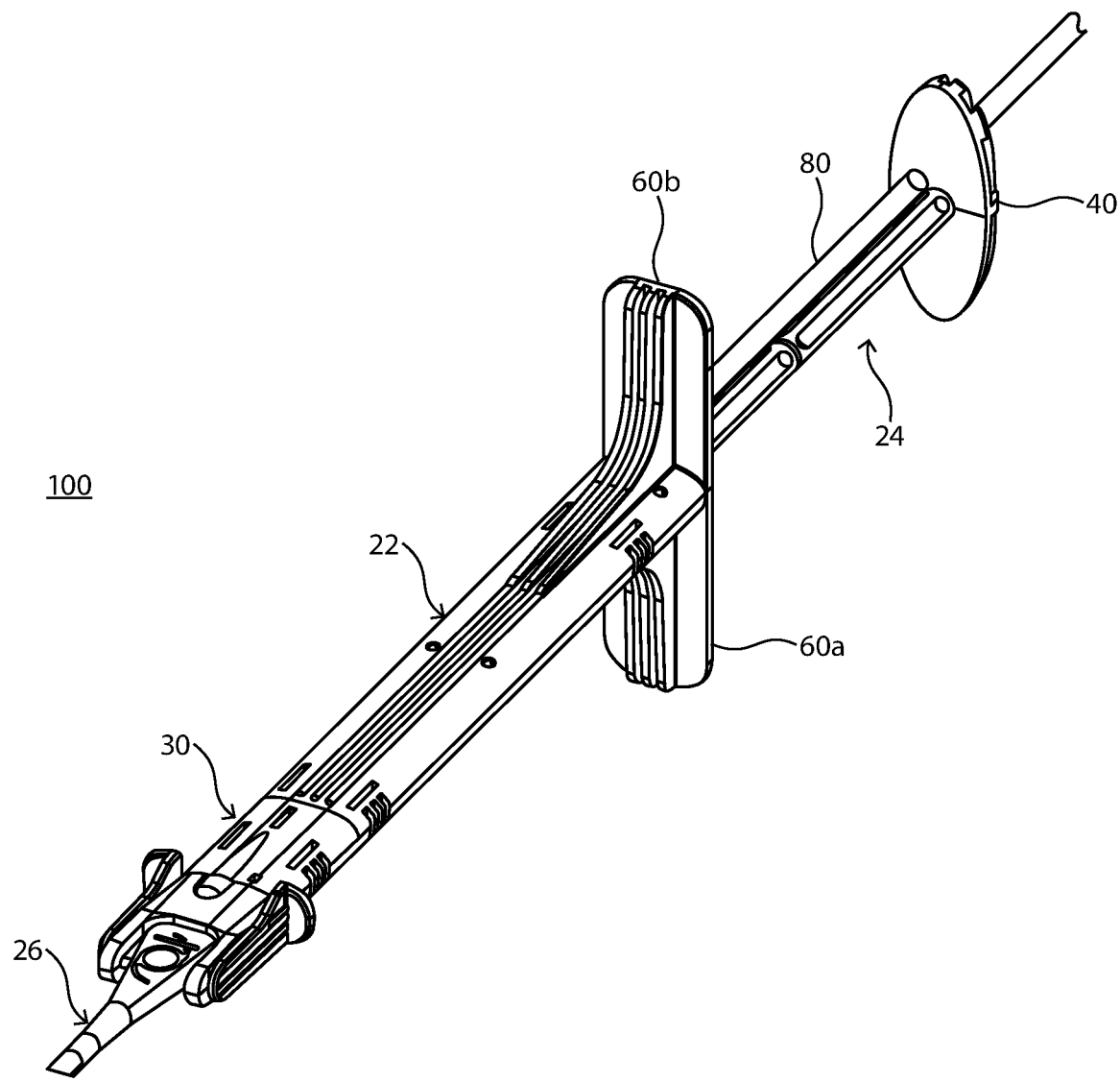
FIG. 1 is an assembled perspective view of an insertion system according to an embodiment of the invention.

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present invention facilitates the process of delivering an intraocular lens (IOL) into a patient's eye using an inserter. The IOL is typically implanted using an injector that rolls, folds, or otherwise configures the lens for delivery through a small incision in the eye in a way that reduces trauma and expedites post-surgery healing. The IOL is stored and transferred to a funnel-shaped delivery tube just prior to delivery. The injector or injector/cartridge is generally used in a manner like a hypodermic needle, with the IOL being injected into the eye through a delivery tube. The injector, cartridge and/or delivery tube may be first partially filled with a liquid or gel lubricating agent, for example a viscoelastic material. These are commonly used techniques for delivering an IOL into a patient's eye, and the present invention will be described in the same context. However, it should be understood that certain principles of the present invention can apply to modified systems, such as those that do not use a syringe-style injector or a funnel-like delivery tube.

Moreover, the present invention provides a system in which an IOL may be inserted using, in part, a mechanical assist to lessen the force needed by the operator of the device to dispense the IOL from the inserter apparatus. Likewise, although various components may be molded together, these components can also be remotely separately and assembled. Also, the insertion systems described herein are especially suited for manipulating leading and trailing haptics of an IOL without the need for skill or training, but certain aspects of the present invention may be applicable to IOLs having haptics that do not require such manipulation. In general, the present invention should not be considered limited to particular IOL insertion configurations except as defined accordingly in the claims.

The present invention may comprise a vacuum-based hydraulic fluid chamber that may aid in reducing the force necessary to successfully eject an IOL from a delivery device. In an embodiment of the present invention, a portion of the push rod may be designed to act as a piston within a chamber associated with the injector device. The piston portion of the push rod may be associated with a sealed chamber area which may be substantially filled with a hydraulic fluid. The hydraulic fluid may be BSS (balanced salt solution) or an open cellular material, such as a foam, for example, that would regulate the motion (dampening) of the piston.

Actuation of the piston may comprise removing the hydraulic fluid from the chamber through at least one valve communicatively connected to the chamber. The valve itself may be communicatively coupled to at least one aspiration/vacuum line to facilitate the removal of the hydraulic fluid from the chamber under at least a partial vacuum. The at least one valve may itself be actuated in response to the movement of the pushrod. For example, the valve may be mechanically associated with the pushrod such that the valve will open to the chamber in an amount commensurate with the force applied to the pushrod (ostensibly by a user of the insertion tool). Similarly, the valve may be electronically controlled, such as through the use of a foot pedal associated with a surgical console. In this way, the movement of the pushrod may be fully and/or partially automated.

In an embodiment of the present invention, the hydraulic chamber may be filled with BSS and a vacuum may be supplied to a valve through an aspiration/vacuum line to facilitate fluid from the hydraulic chamber through the valve when open to pull the push rod towards the distal end of the tool. The valve is opened as the push rod is moved forward by a user of the tool (typically by using one's thumb on the thumb cap at the proximate end of the push rod). The amount of force provided by the removal of the hydraulic fluid is dependent of the strength of the vacuum provided and the amount the valve is opened and may be proportional to the amount of force provided by the user on the push rod. For example, the more force applied to the thumb of the plunger, the more assist is applied to the hydraulic piston. As force is released from the thumb of the plunger, the valve may close and the hydraulic assist may stop.

Preferably, the vacuum is held substantially constant such that a linear relationship exists between the force provided by the user and the removal of the hydraulic fluid. As would be appreciated by those skilled in the art, the varying of the vacuum pressure may allow for customized control over the amount of force provided by the piston drive system discussed herein. For example, the hydraulic assist may be used for a small amount of linear travel by the push rod (such as pushing the IOL to near the distal end of the insertion tip) and may therefore be relatively compact.

FIG. 1 illustrates an exemplary IOL insertion system 100 of the present invention comprising a syringe-style device having, generally, a handpiece 22, a plunger 24, an aspiration line 80, and a delivery tube 26 on a distal end thereof. The system 100 is also shown exploded in FIG. 2.

Figure 2:
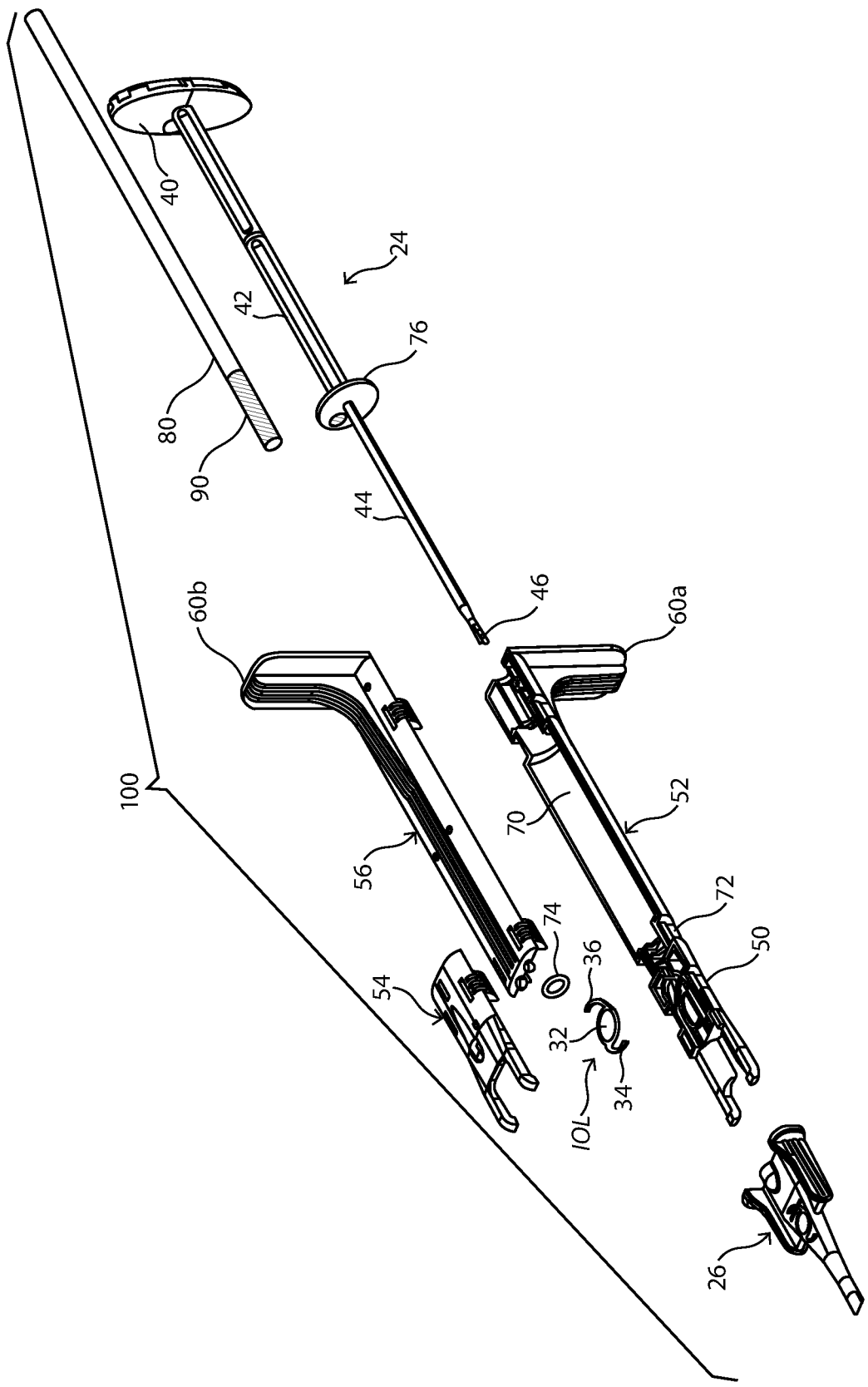
FIG. 2 is an exploded perspective view of the insertion system of FIG. 1.

The IOL is shown in FIG. 2 positioned between two halves of a holding station 30 (as shown in FIG. 1). The IOL may comprise a central circular optic 32 having a leading haptic 34 and a trailing haptic 36 generally spirally extending therefrom. The present invention is especially suited for manipulating this particular configuration of IOL, although certain aspects of the invention may be applicable to other IOLs.

With reference to FIGS. 1 and 2, the system 100 defines a longitudinal axis from the plunger 24 at a proximal end to the delivery tube 26 at a distal end. The plunger 24 includes a thumb cap 40, a piston rod 42, a narrower push rod 44 fixedly connected to and extending from the piston rod, and a distal tip 46. In the illustrated embodiment, the distal tip 46 is forked to enable reliable capture of a proximal edge of the IOL optic 32. The plunger 24 translates axially through an elongate passage defined within the inserter handpiece 22 and is configured to urge the IOL from a holding station 30 through the distal delivery tube 26. In a general sense, the plunger 24 represents any actuator capable of displacing the IOL from the holding station 30 in a distal direction through a delivery tube or other such device. The plunger 24 therefore may be generally termed an actuator so as to encompass other prime movers that can perform the same function, such as rotary actuators, threaded actuators, levers, pistons, etc.

The lower half of the holding station 30 comprises a base 50 that, in a preferred embodiment, forms a distal extension of a base portion 52 of the handpiece 22. The upper half of the holding station 30 comprises a cover 54 that abuts a top portion 56 of the inserter handpiece 22. In the illustrated embodiment, as seen in FIG. 1, the cover 54 and top portion 56 fit directly over the base 50 and base portion 52 to form the elongated handpiece 22. The overall shape of handpiece 22 may be somewhat flattened in a plane parallel to the interface between the upper and lower components. For example, the handpiece 22 may be configured to have an external aspect ratio in a cross-sectional plane perpendicular to the longitudinal axis of at least 1.5, at least 2, or at least 2.5 over a predetermined length parallel to the longitudinal axis, the predetermined length being greater than 50 percent or greater than 75 percent of the total length of the handpiece 22. As seen in FIG. 2, the IOL optic 32 may be positioned approximately at a horizontal midplane of the inserter handpiece 22, which plane also defines the orientation of handpiece.

The handpiece further includes a pair of proximal finger tabs 60a, 60b, one on the base portion 52 and one on the top portion 56. When an operator desires to depress the plunger 24, he or she may place the thumb of one hand on the thumb cap 40, and index and middle fingers on respective finger tabs 60a, 60b. Squeezing the hand closed depresses the thumb cap 40. The flattened orientation of the inserter handpiece 22 may be ergonomically designed to lessen the profile between the index and middle fingers and thus enhance comfort. The flattened nature of the handpiece 22 also provides torque leverage so that the operator can more easily rotate the handpiece about its longitudinal axis.

The exploded view of FIG. 2 further shows a hydraulic chamber 70 in the handpiece base 52 for receiving the piston rod 42 and push rod 44. A similar mating channel is also provided on the underside of the handpiece top portion 56 with the base portion 52 comprising a rubber seal (not shown) sufficient to allow hydraulic chamber 70 to contain a liquid under pressure. Semi-circular groove 72 (provided at the distal end of the base 52) (and a similar mating groove on the underside of the top portion 56) receives at least one O-ring 74 which may form a liquid tight seal around a portion of push rod 44.

The piston rod 42 includes a large oblong rubber piston head 76 spaced along its length that registers with the proximate end of hydraulic chamber 70. Specifically, the piston head 76 has an outer diameter equal to or slightly larger than the inner diameter of the hydraulic chamber 70 so as to provide a liquid tight seal as piston rod 42 is advanced. Valve 90 may be in communication with the face of piston head 76 and may in communication with piston rod 42. Specifically, the forward movement of piston rod 42 may open valve 90 and allows for liquid contained in the hydraulic chamber 70 to be drawn out of the chamber and into aspiration tube 80.

Valve 90 may be a proportional valve and may be alternatively located at the console or may be an in-line valve associated with a handpiece as described above. IT a proportional valve is associated with a handpiece, the value may be located proximate to a handpiece and may, preferably, be located near the terminal end of the aspiration/vacuum tube. Location of the valve may be dictated by cost concerns. More specifically, a larger (and presumably less expensive) valve may be more suitably placed away from the handpiece, remaining proximate to the console. However, a valve placed at the terminal end of the aspiration/vacuum line may provide for greater control over the delivery of fluid, for example, and may provide precise control and flow up to at least 0.01 ml to 5 ml/sec. A suitable valve may exceed those guidelines within the ISO 10993-1:2009 matrix and LSP regulatory standards for bio-compatibility. Additionally, the valve may be a two-way valve or a three-way valve, for example, allowing actuation by the push rod, providing a release to vent, and allowing pull back to reverse pressure to a dampener. In this way, lens delivery may be moved forward, held mid-delivery, even reversed should that become necessary.

The hydraulic chamber 70 may be filed with hydraulic fluid prior to use by a user. Providing a "pre-loaded" syringe may allow, for example, other fluids to be used as the hydraulic fluid which may not otherwise be readily available to the user of the tool at the place or time of use. In an embodiment of the present invention, the hydraulic chamber 70 may be filled by the user prior to loading of the IOL. For example, fluid may be drawn in to the chamber 70 through narrower push rod 44 by forwarding plunger 24 to near its fully actuated position and drawing fluid from holding station 30 into chamber 70 through at least one channel provided in association with narrower push rod 44. Once the plunger 24 is fully retracted, any air pockets which may exist in the otherwise full chamber 70 may be expelled by forwarding the plunger 24 slightly while the tool is in a vertical position. Alternatively, for example, the distal end of the delivery tube may be placed in contact with the hydraulic fluid, such as using a cup or reservoir, using the same technique described above to fill the chamber.

The filling of chamber 70 may also be accomplished through valve 90, for example, and a special filling tool, not shown, may be used to fill the chamber through the valve. As would be appreciated by those skilled in the art, the valve may allow for the introduction of a hydraulic fluid through the use of a bottle which may include a small plastic funnel attachment the may actuate the valve when engaged to allow for the contents of the bottle (presumably BSS) to be dispensed into the chamber. Another method might be to use Irrigation pressure to the chamber, since the fluid is needed for the surgical procedure and is readily available.

Figure 3:
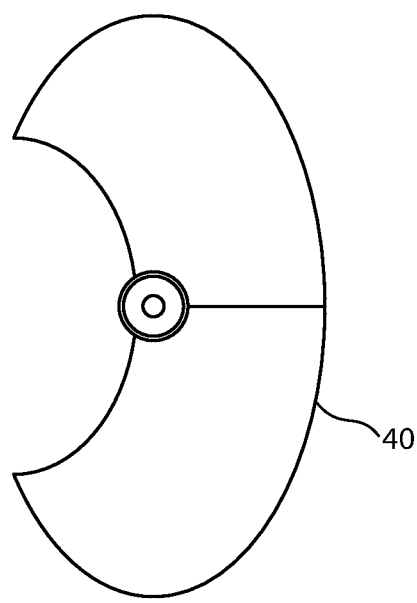
FIG. 3 is a plain view of a thumb cap embodiment in accordance with the present invention.

In an embodiment of the present invention, as illustrated in FIG. 3, a thumb cap for use with the present invention may be partially hollow to allow for the passage of lines (for example, an aspiration line or a valve control wire) from the handpiece to a console in a linear fashion to limit and disruption of operation by the user.

In an embodiment of the present invention, the aspiration line from the console may be communicatively coupled to the chamber of the handpiece through, for example, any aspect if the handpiece such as the top portion, for example. Further, the aspiration line may also allow for pressurization and may, for example, provide for a reverse flow of either the removed hydraulic fluid, or for the introduction of a gas, such as air. In this way, the piston may be reversed.

In an embodiment of the present invention, the hydraulic chamber may at least partially comprise a solid which may be, for example, a cellular foam or other porous substance. Such a filing may itself be compressible and may provide a dampening effect on the movement of the plunger. For example, a compressible cellular foam filled with BSS may allow for the extraction of the BSS to engage the hydraulic function of the present invention, while providing a consistent compression factor which may, for example, provide more consistent rate of travel of the push rod. Similarly, as with each embodiment, the use of hydraulic pressure may positively affect the static positioning of the push rod when force from a user is released or lessened.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. An intraocular lens insertion system comprising:
    an insertion rod comprising a tube having a first end and a second end;
    a piston head affixed to the insertion rod and positioned between the first end and the second end;
    a hydraulic chamber;
    an aspiration line communicatively connected to the hydraulic chamber; and
    at least one valve in fluid communication with the aspiration line;
    wherein at least a partial vacuum is applied to the aspiration line,
    wherein the insertion rod moves in response to the at least a partial vacuum to displace hydraulic fluid within the hydraulic chamber.

2. The system of claim 1, wherein the at least one valve is proximate to the piston head.

3. The system of claim 1, wherein the at least one valve is a proportional valve.

4. The system of claim 1, wherein the at least one valve opens in response to the movement of the insertion rod.

5. The system of claim 1, wherein the at least one valve is electronically controlled.

6. The system of claim 1, wherein the at least one valve is controlled via a foot pedal device.

7. The system of claim 1, wherein the at least one valve is communicatively coupled to the piton head.

8. The system of claim 1, wherein a portion of the hydraulic fluid is removed from the hydraulic chamber through the aspiration line.

9. The system of claim 1, wherein an outer edge of the piston head creates a seal along at least a portion of the hydraulic chamber.

10. The system of claim 1, wherein the second end is suitable for engaging an intraocular lens.

11. The system of claim 1, wherein the first end comprises a thumb cap.

12. The system of claim 1, wherein the insertion rod is solid.

13. The system of claim 1, wherein the insertion rod is at least partially hollow.

14. The system of claim 1, wherein the insertion rod is non-round.

15. The system of claim 1, wherein the hydraulic fluid comprises a balanced salt solution.

16. The system of claim 1, wherein the hydraulic chamber comprises at least one foam.

17. The system of claim 1, wherein a positive pressure is introduced into the hydraulic chamber.

18. A method of inserting an intraocular lens, the method comprising:
    applying a first force on an insertion rod comprising a tube having a first end and a second end;
    applying a second force on the insertion rod;
    wherein the first force is applied at the first end of the insertion rod and the second force is applied at a piston head affixed to the insertion rod;
    wherein the piston head is positioned between the first end and the second end; and
    wherein the second force is created by hydraulic pressure comprising at least a partial vacuum.

19. The method of claim 18, wherein the second force is controlled by at least one valve.

20. The method of claim 18, wherein the insertion rod moves in response to one selected from the group consisting of a first pressure, a second pressure, and combinations thereof.

* * * * *